United States Patent [19]

Krebser et al.

[11] Patent Number: 5,010,452
[45] Date of Patent: Apr. 23, 1991

[54] THERAPEUTIC LAMP FOR BIOSTIMULATION WITH POLARIZED LIGHT

[75] Inventors: Werner Krebser, Embrach, Switzerland; Michael Lantos, Budapest; Peter Kolta, Pécs, both of Hungary

[73] Assignee: Harrier GmbH Gesellschaft fur den Vertrieb medizinischer und technischer Gerate, Fed. Rep. of Germany

[21] Appl. No.: 348,008

[22] PCT Filed: Oct. 7, 1988

[86] PCT No.: PCT/EP88/00900
§ 371 Date: Apr. 14, 1989
§ 102(e) Date: Apr. 14, 1989

[87] PCT Pub. No.: WO89/03236
PCT Pub. Date: Apr. 20, 1989

[30] Foreign Application Priority Data

Oct. 7, 1987 [DE] Fed. Rep. of Germany ........ 3733905
Sep. 16, 1988 [DE] Fed. Rep. of Germany ..... 88115249

[51] Int. Cl.$^5$ ................................. F21V 9/14
[52] U.S. Cl. ...................... 362/19; 362/294; 362/373; 362/346; 128/396
[58] Field of Search .................. 362/346, 19, 294, 373, 362/298, 300, 345, 804; 128/395, 396

[56] References Cited

U.S. PATENT DOCUMENTS 3,936,686 2/1976 Moore ................................. 313/36
4,663,698 5/1987 Tomlinson ......................... 362/346
4,682,276 7/1987 Miller ................................. 362/294

FOREIGN PATENT DOCUMENTS 0148144 7/1985 European Pat. Off. .
3220218 3/1983 Fed. Rep. of Germany .
859067 12/1940 France ................................. 362/19
84/03049 8/1984 PCT Int'l Appl. .

Primary Examiner—Stephen F. Husar
Assistant Examiner—D. M. Cox
Attorney, Agent, or Firm—Michael N. Meller

[57] ABSTRACT

A therapeutic lamp for biostimulation with polarized light, which comprises a light source with a power substantially between 30W and 300W, a reflector with a rotational paraboloid light reflecting surface arranged behind the light source so that the focal point substantially coincides with the point source, a polarizer arranged in the path to generate polarized output light which has a cross-section of at least 100 cm$^2$. The lamp further comprises a first tube with a first axis coinciding with axis of rotation of the paraboloid surface, the reflector with the light source is fixed in the first tube so that a sealed connection is provided therebetween, a second tube with a second axis which closes an angle between 110° and 120° with the first axis, the tubes have substantially equal and circular cross-sections and are attached to each other to form an integral housing.

11 Claims, 4 Drawing Sheets

THERAPEUTIC LAMP FOR BIOSTIMULATION WITH POLARIZED LIGHT

The invention relates to a therapeutic lamp for biostimulation with polarized light, which comprises a light source with a power substantially between 30W and 300W and which is substantially a point source, a reflector with a rotational paraboloid light reflecting surface defining a focal point arranged behind the light source so that the focal point substantially coincides with the point source to reflect forward the majority of light emitted by the source in a parallel path, a polarizer arranged in said path to generate polarized output light propagating in a predetermined direction and which has a cross-section of at least 100 cm$^2$.

The term "therapeutic" should be interpreted in broad sense which covers all applications of biostimulation for which polarized light can be used.

A therapeutic lamp of the kind defined is already known e.g. from the published European patent application 84850395.

German patent No. 32 20 218 C2 describes the general biostimulating effects of polarized light. The lamp described in the example of that patent can provide an output light bundle with parallel rays and with a circular cross-section which has a diameter of about 50 mm and the lamp power is about 150W. The lamp generates much heat which is transported away by means of a fan. All optical elements of that embodiment are arranged linearly after one-another.

In the international publication WO 84/03049 a therapeutic lamp of the kind defined is described which represents a more improved design. Here a Brewster-type polarizer is used which is effective also in the infrared range of wavelengths. Owing to the utilization of the infrared spectral components of the bulb a substantial reduction of the required lamp power could be attained. The use of a Brewster-type polarizer requires that the passageway of the light beams be tilted in a predetermined angle, in which the direction of the output beams close an angle of 114° (the twice of Brewster's angle) with the main direction of the light source. This requirement substantially affects the form of such lamps. In the above referred type of the lamp a substantially cylindrical case was used which comprised a separate handle portion and an obliquely directed frontal portion. In the frontal portion specific filter elements and a glass plate were provided to prevent the surface of the polarizer from the dust present in the sucked-in air. The cooling of the case was provided by a fan and it was designed in such a way that the casing remained substantially open which could not safely prevent the sensitive light reflecting or transpassing surfaces from getting dusty with time.

The cross-section of the output light of such a therapeutic lamp can not be increased without difficulties. If the cross-section is increased, the cooling used so far gets rapidly insufficient or if the airflow of the fan is increased, then the danger of dust formation on the optical surfaces also increases. With increased light cross-section the volume and weight of the lamp can be substantially higher which makes the holding and positioning of the lamp more difficult. The operation of the lamp requires the use of a separate power supply.

The aforementioned European published patent application 84.850.395.9 describes a different kind of therapeutic lamp which is designed for providing larger light cross-sections. This lamp comprises a housing arranged in the lower part of the device which is similar to the widely used overhead projectors. The upper surface of the housing is made by a Fresnel lens. In the housing there is provided a metal halogen lamp with a higher power i.e. between about 200 to 800W and the lamp is arranged in the focal line of the Fresnel lens. A parabolic reflector surface is provided below the lamp to reflect the backwardly radiated rays towards the lens. In the housing an intensive cooling is provided by means of a fan. The device comprises a Brewster polarizer arranged as a separate unit fixed to the upper rear edge of the box-like housing and extends obliquely in upward and forward direction. The weight and volume of such a lamp is high and the intensive cooling makes disturbing noise and heat. Owing to the open design the optical surfaces are exposed to dust and dirt.

For several therapeutic applications it is sufficient if the cross-section of the polarized light bundle has a square dimension of about 100 through 300 cm$^2$. For such applications there is a need for a quietly operating therapeutic lamp which can be handled easily and in which the possibility of dust formation is highly reduced.

The object of the invention is to provide a therapeutic lamp with such properties, i.e. which has a static cooling, in which dust building is practically eliminated and which enables an easy handling.

A further object of the invention is to provide such a lamp with reduced manufacturing costs and without the need of a separate power supply and electronic unit.

A further object is the need for extending the expected lifetime and for increasing the effectiveness of biostimulation.

According to the invention a therapeutic lamp has been provided for biostimulation with polarized light, which comprises a light source with a power substantially between 30W and 300W and being substantially a point source, a reflector with a rotational paraboloid light reflecting surface defining a focal point arranged behind the light source so that the focal point substantially coincides with the point source to reflect forward the majority of light emitted by the source in a parallel path, a polarizer arranged in the path to generate polarized output light propagating in a predetermined direction and which has a cross-section of at least 100 cm, in which the improvement is that the lamp furthermore comprises a first tube with a first axis coinciding with axis of rotation of the paraboloid surface, the reflector with the light source is fixed to the first tube so that a sealed connection is provided therebetween, a second tube with a second axis which closes an angle between 110° and 120° with the first axis, the tubes have substantially equal and circular cross-sections and are attached to each other to form an integral housing, both of the tubes are cut with a plane extending normal to a plane determined by the first and second axis, so that the plane cuts substantially the whole cross-sections of both tubes, the cutting plane closes substantially the same angle with the first and second axis, whereby an opening with an elliptical contour line is defined, a light diverting means closing the opening for diverting light arriving from the first tube to axial direction of the second tube, the means comprises a closing plate of a heat conducting material and has a heat dissipating increased rear surface, a light transparent plate is arranged in a frontal section of the second tube to close and seal the inner space thereof, and static heat dissipating means which contacts the reflector for providing operational temperature for the light source.

This basic design is useful, since the effective utilization of the lamp output enables the use of a smaller lamp power, and the large diameter of the tubes provide a static cooling in combination with the large reflector surface and large surface of the closing means. The static cooling enables that the optical elements can be arranged within a closed space which reduces the problems of sdust, and on the other hand there will be no need for double walls with air cooling channels, whereby the volume and weight will be minimized.

In a preferable embodiment the light diverting means comprises the polarizer which is a Brewster polarizer, and the angle defined between the axes of the first and second tubes is twice of Brewster's angle i.e. about 114°.

In that embodiment the Brewster polarizer comprises a plurality of spaced thin plano-parallel glass plates which substantially cover the cut opening.

It is preferable if the light source is a metal halogen bulb.

For the precise positioning of the bulb a socket is provided for receiving the bulb, the socket is fixed in a mount made of a heat conducting material, the mount can have a cylindrical and a slightly conical outer surface to enable fine positioning of the bulb.

The reflexion properties will improve if the reflector is made of an aluminum alloy comprising 22 to 35 Vol % zinc and 0.3 to 0.6 Vol % iron.

It is preferable if the static heat dissipating means is provided on the reflector in the form of cooling rings, and the reflector comprises an axial bore for receiving the mount.

The light will be softer and less disturbing if the transparent plate is a light filter plate transparent for wavelength components exceeding 400-450 nm.

The spectral distribution of the lamp can be shifted to a biologically favorable range if the bulb is underheated so that while operating the color temperature thereof is between about 3000 and 3200° K.

In a further embodiment of the lamp the tubes form parts of an integral plastic housing, the housing comprises a round bar which encircles the frontal and upper half of the second tube and extends downwardly substantially parallel to the first axis in the form of a pair of spaced legs and it is continued in the form of horizontal rods, the first tube comprises a hollow rectangular portion which extends along frontal zone of the first tube and ends in the second tube, a horizontal projection extends out of the bottom of the rectangular portion to receive ends of the horizontal rods, the first tube includes the reflector and the heat dissipating means and it has a bottom end normal to the first axis.

The utilization of the available space gets better if a toroid transformer for supplying the light source with a small voltage is arranged in the first tube below the paraboloid surface and electronic circuits for operating the light source are arranged in the hollow space of the rectangular portion of the first tube.

The manufacture will be easier if the reflector is made of a thin metal sheet and the heat dissipating means comprises a member made of a heat conducting metal fitting in the interior of the first tube and the member has an upper recess in conformity with the shape of the rear side of the reflector, and these conforming surfaces are attached to each other so that a good heat conductive coupling is established between them, cooling grooves are provided at the cylindrical outer periphery of the member, and a central bore is formed in the member for receiving a mount which holds the light source, and a toroidal recess is formed at the bottom of the member to receive the toroid transformer.

The operational properties will improve if the electronic circuits comprise a timer for adjusting length of lighting periods of the light source and a circuit for providing delayed rising of the current through the light source.

It is also preferable if the rectangular member is made of an aluminum alloy and it has a cylindrical bottom part extending to the bottom of the first tube and a metal closure plate is attached to the bottom of the first tube to close the hollow cavity thereof, and the closure plate is provided with cooling grooves.

In a first alternative of this embodiment the light diverting means comprises the polarizer which is a Brewster polarizer, and the angle defined between the axes of the first and second tubes is twice of Brewster's angle i.e. about 114°, and the transparent plate is a light filter plate transparent for wavelength components exceed 400-450 nm.

In a second alternative embodiment the light diverting means comprises a mirror and the transparent plate is a polarizer filter and it is preferable if the filter is effective also in the infrared range of wavelengths.

The invention will now be described in connection with preferable embodiments thereof, in which reference will be made to the accompanying drawings. In the drawing.

In the first embodiment of the invention shown in FIGS. 1 to 6 a therapeutic lamp 1 comprises a pair of cylindrical metal tubes 2 and 3 welded together and the axes thereof close an angle of about 114° which corresponds to the twice of Brewster's angle. The rear portion of the two tubes 2, 3 is cut in a common plane and a Brewster type polarizer 4 covers the cut hole which has an elliptical contour.

Figure 4:
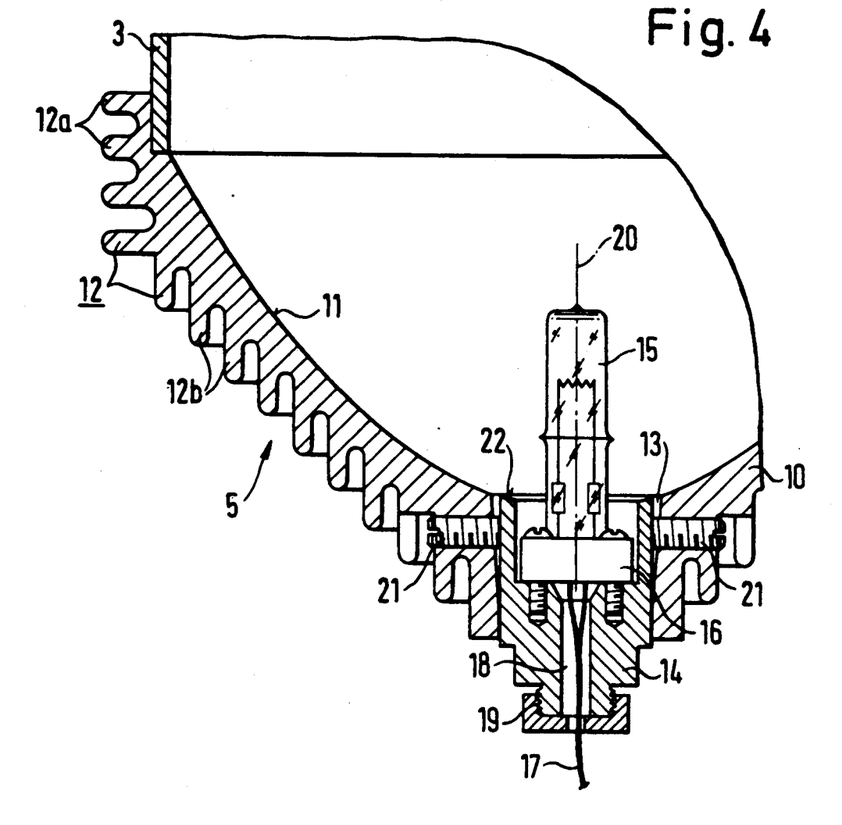
FIG. 4 is a sectional elevational view of the reflector assembly.
Figure 5:
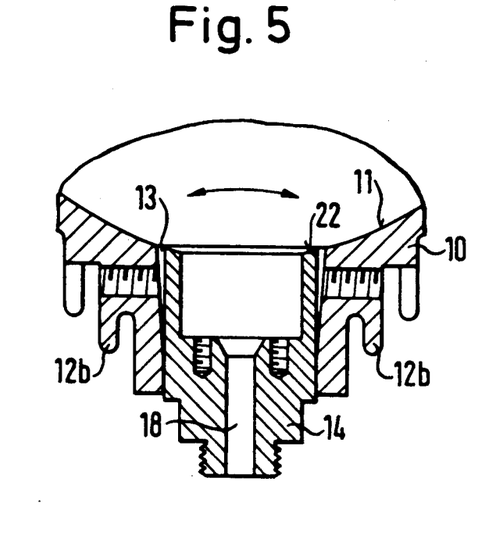
FIG. 5 shows the enlarged sectional view of the bottom part of the reflector assembly.

A reflector assembly 5 is attached to the free (lower) end of the tube 3 an FIGS. 4 and 5 show detailed internal structure thereof.

Figure 1:
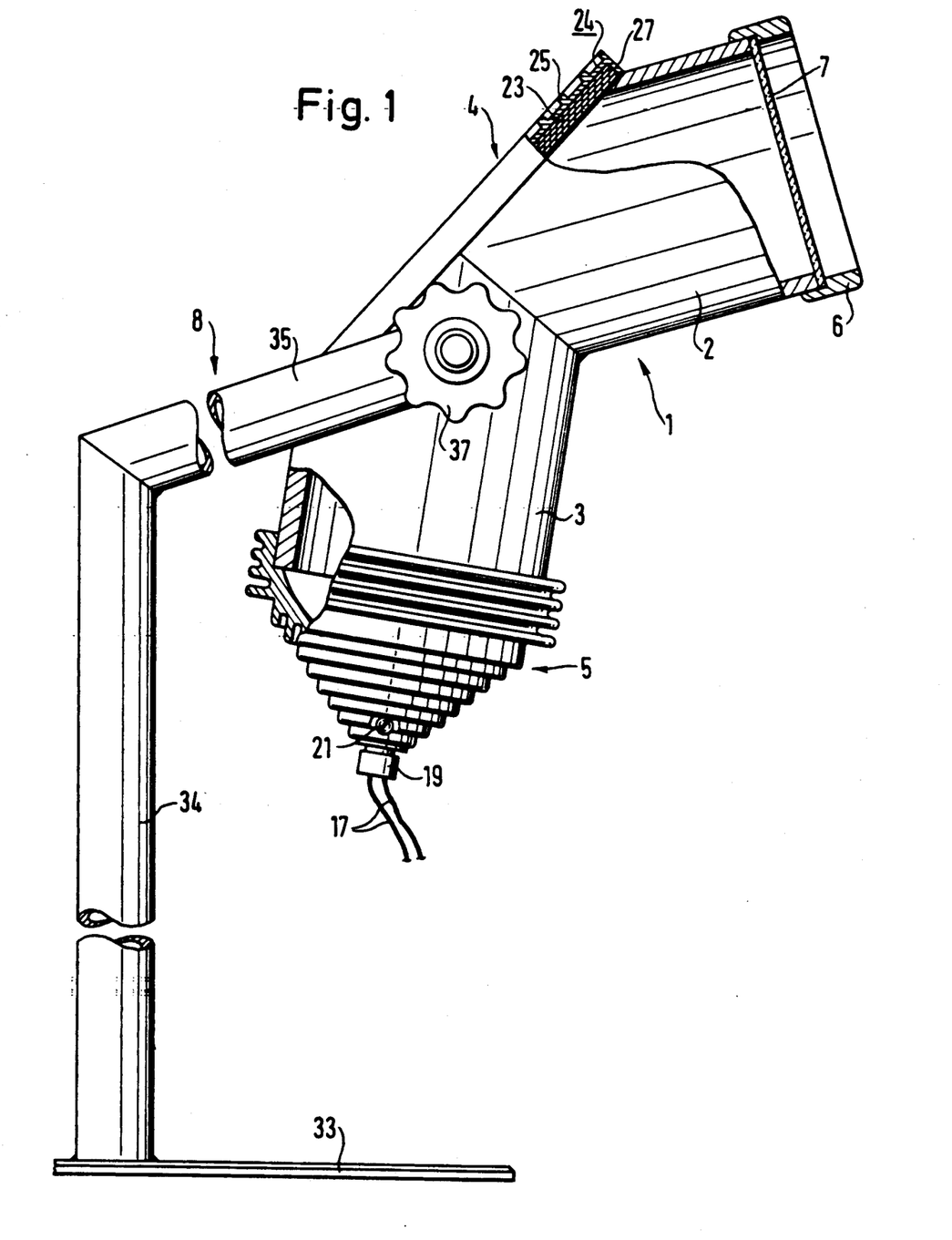
FIG. 1 shows the elevation view of the first embodiment of the invention, partly in section.

The frontal end of the tube 2 is closed by sleeve 6 in such a way that a light filter plate 7 is pressed between the end face of the tube 2 and the sleeve 6. It is preferable if the light filter plate 7 is made of a yellow filter which is transparent only for the spectral components with wavelength exceeding about 400-450 nm. The plate 7 seals the internal space of the therapeutic lamp 1.

Figure 6:
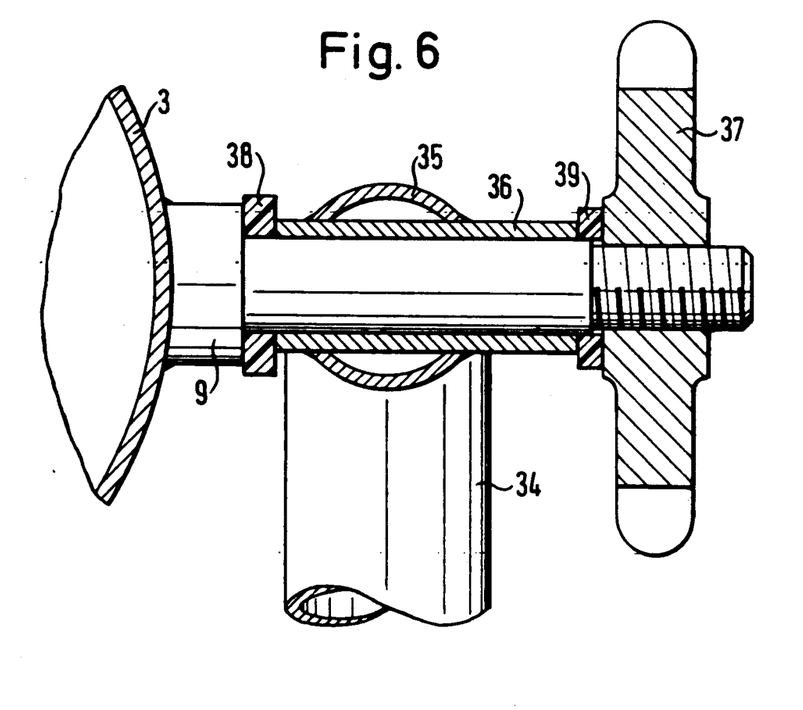
FIG. 6 shows a detail in section of the connection of the support tube 34 to the tube 3.

FIG. 1 shows support device 8 which is in engagement with a threaded bolt 9 welded to the side of the tube 3 as shown in FIG. 6.

With reference to FIGS. 4 and 5 the structure of the reflector assembly 5 will be described. The reflector assembly 5 comprises reflector 10 being die-cast of a specific aluminum alloy followed by a machining. The reflector 10 has a polished internal paraboloid surface 11 and in a preferable embodiment the largest diameter thereof is 140 mm. A ring-like shoulder is provided on the reflector 10 at the frontal edge of the paraboloid recess which serves as an abutting surface for the end of the tube 3, like illustrated in FIG. 4. The reflector 10 is provided with several concentrically arranged cooling rings 12 from which rings 12a are normal to rings 12b. It can be understood that the rings 12 can be arranged in other configurations as well.

The reflector 10 comprises a central bore 13 which includes a short cylindrical section followed by a longer conical section.

The reflector 10 is casted of an aluminum-zinc alloy comprising about 22 to 35% zinc and it is preferable if the alloy comprises iron in an amount of about 0.3 to 0.6%. A preferable composition comprises 30% zinc, 0.4% iron and the rest is aluminum. These values should be interpreted in volume percents. Such a composition has surprisingly favorably properties.

The bore 13 is adapted to receive a mount 14 for holding light source 15 being preferably a metal halogen bulb with a nominal power of 50W. The light source 15 has a short filament, therefore it can be regarded as a point source. The light source 15 is inserted in a standard socket 16 which latter is fixed in the mount 14 by means of bolts. The electrical wires 17 lead out of the light source 15 are lead through central bore 18 of the mount 14. These wires are fixed by clamping member 19 attached to the rear end of the mount 14.

The light source 15 is arranged in such a way within the reflector 10, that the filament thereof coincides with the focal point of the paraboloid surface 11. The scale of FIG. 4 is practically 1:1 and it can well be observed in this figure that the mouth of the paraboloid surface 11 is far ahead of the focal point. This arrangement ensures that the paraboloid surface 11 reflects a major portion of the light of the light source 15 in forward direction parallel to the axis of rotation 20. For a more complete utilization of the available light output the ring-shaped forward face 22 of the mount 14 is formed as a continuation of the paraboloid surface 11 and it is polished as well. The mount 14 can also be made by an appropriate aluminum alloy.

The filament can be precisely adjusted in the focal point by means of four adjusting bolts 21. The picture of the filament should be projected to a remote surface and the optimum position can be reached by adjusting the position of the mount 14 in the conical portion of the bore 13. By means of such an adjustment the manufacturing tolerances in the position of the filament of the mass-produced bulb can be corrected. The mount 14 can be shifted both in forward and backward direction and the structure allows a slight tilting movement as well. By fastening the adjusting bolts 21 the position of the mount 14 can be fixed in the adjusted optimum.

Figure 2:
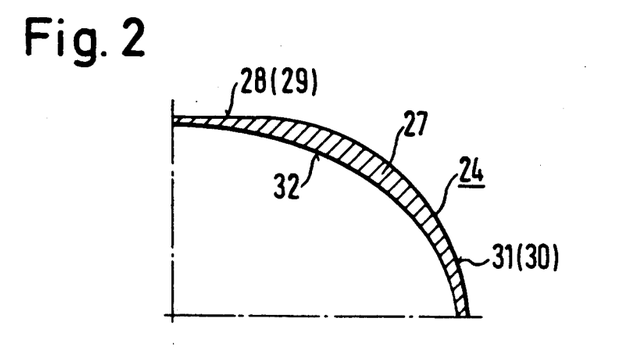
FIG. 2 shows a quarter of the closing plate 24 in section.
Figure 3:
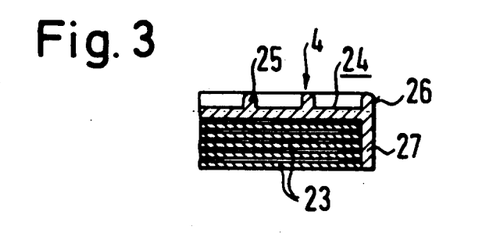
FIG. 3 is an enlarged sectional detail through the Brewster polarizer.

The structural design of the Brewster polarizer 4 will now be described with reference to FIGS. 1 to 3. The Brewster polarizer 4 comprises a few number (e.g. five) thin plano-parallel glass plates 23 which have elliptical form and are spaced from one-another. A closing plate 24 is arranged behind the glass plates 23 which can be made of a die-cast aluminum alloy and the closing plate 24 is attached to the tubes 2, 3 to provide a sealed closure for the elliptical opening. For attaining increased heat transfer the inner surface of the plate 24 is made black e.g. by electrolytic plating. The spacing between the respective glass plates 23 and between the rear glass plate and the closing plate 24, as well as between the so-obtained assembly and the elliptical cut surface of the tubes are provided by thin plastic stripes.

The outer surface of the closing plate 24 i.e. which is at the opposite side of the plate relative to the glass plates 23 is provided with elongated cooling ribs 25 which extend substantially parallel to outer edge 26 of the closing plate 24. In a preferable embodiment the outer edge can be made as a downwardly projected flange 27. A sectional view of a quarter of the flange 27 is shown in FIG. 2. The outer edge or contour line 26 of the closing plate 24 is defined by a pair of parallel lines 28, 29 and a pair of circular arc sections 30, 31. Owing to the fact that the oblique cut surface of the tubes 2, 3 has an elliptical form, the width of the flange 27 is not uniform. The inner contour line 32 or edge of the flange has an elliptical form which corresponds to the form of the glass plates 23 and to that of the cut surface. Such a spatial design of the closing plate 24 can provide an aesthetically pleasing appearance for the connection and closure of the two tubes 2,3.

The support device 8 comprises a wide foot plate 33 (see FIG. 1), a support tube 34 welded on the foot plate, a console tube 35 attached obliquely to the end of the support tube, and a positioning device arranged at the free end of the console tube. The positioning device comprises a sleeve 36 lead through a pair of opposite holes made in the side of the console tube 35 and fixed in this position. The support bolt 9 of the therapeutic lamp 1 is fitted in this sleeve 36, whereby a cylindrical bearing is provided. The bolt 9 has a threaded frontal section which engages an adjustment wheel 37. At the ends of the sleeve 36 washers 38, 39 of soft and low friction material are provided. The therapeutic lamp 1 can be fixed by fastening the adjustment wheel 37 in any adjusted position.

The operation of the first embodiment of the therapeutic lamp 1 according to the invention is as follows:

The light source 15 emitts visible and infrared light which is directed by the reflector assembly 5 forward in axial direction so that the angle of incidence of the light on the Brewster polarizer 4 is equal to 57°. The glass plates 23 of the Brewster polarizer 4 reflect light in the direction of the axis of the tube 2 and this light is linearly polarized. The non-reflected portion of the light hits the black inner surface of the closing plate 24 and the heat generated thereby will be radiated away by the cooling ribs of the plate. Owing to the robust design and the high thermal conductivity of the closing plate 24, this latter will have constant a temperature with uniform distribution.

A standard metal halogen bulb has a color temperature of about 3400° K. when supplied by the nominal voltage. For the purposes of biostimulation it can often be more preferable if the color temperature is adjusted to a somewhat lower value e.g. about 3000°–3200° K., since in case of a lower color temperature the spectral distribution of the radiated light is shifted towards the infrared range. Infrared light has a higher depth of penetration into the living tissues than visible light has. The lower color temperature can be provided by a slight underheating of the light source 15, whereby the expected life time of the bulb will be increased significantly.

The selection of the aforementioned composition for the material of the reflector 10 is preferable has been chosen for the following reasons: In polished state this zinc alloy has excellent reflexion properties and these properties remain unchanged during a long period of time. Such property is rather unexpected in case of an aluminum alloy, which generally looses surface brightness with time due to corrosion. The material is well workable and has a good castability and due to such properties the paraboloid surface 11 can be provided easily. Since the paraboloid surface 11 effectively reflects forward the incident light beams, on the first hand the amount of heat which should be dissipated by the reflector 10 will be smaller and on the other hand a bulb with a smaller nominal power can be used to provide a predetermined intensity. The heat which should be radiated away by the cooling rings 12 of the reflector is small compared to the large surface of the rings, and in case of a lamp power of 50W and a inner tube diameter of 140 mm, the temperature increase of the reflector compared to the ambient temperature will always be below 20° C. even after a longer time of operation. Such a therapeutic lamp radiates polarized light with a diameter of 140 mm and the light intensity measured in a plane about 200 mm from the end of the sleeve 6 is about 50 mW/cm$^2$.

If the power of the lamp is increased, the geometrical sizes will be increased to a corresponding extent, and the favorably properties remain substantially unchanged up to a lamp power of about 200W.

Figure 7:
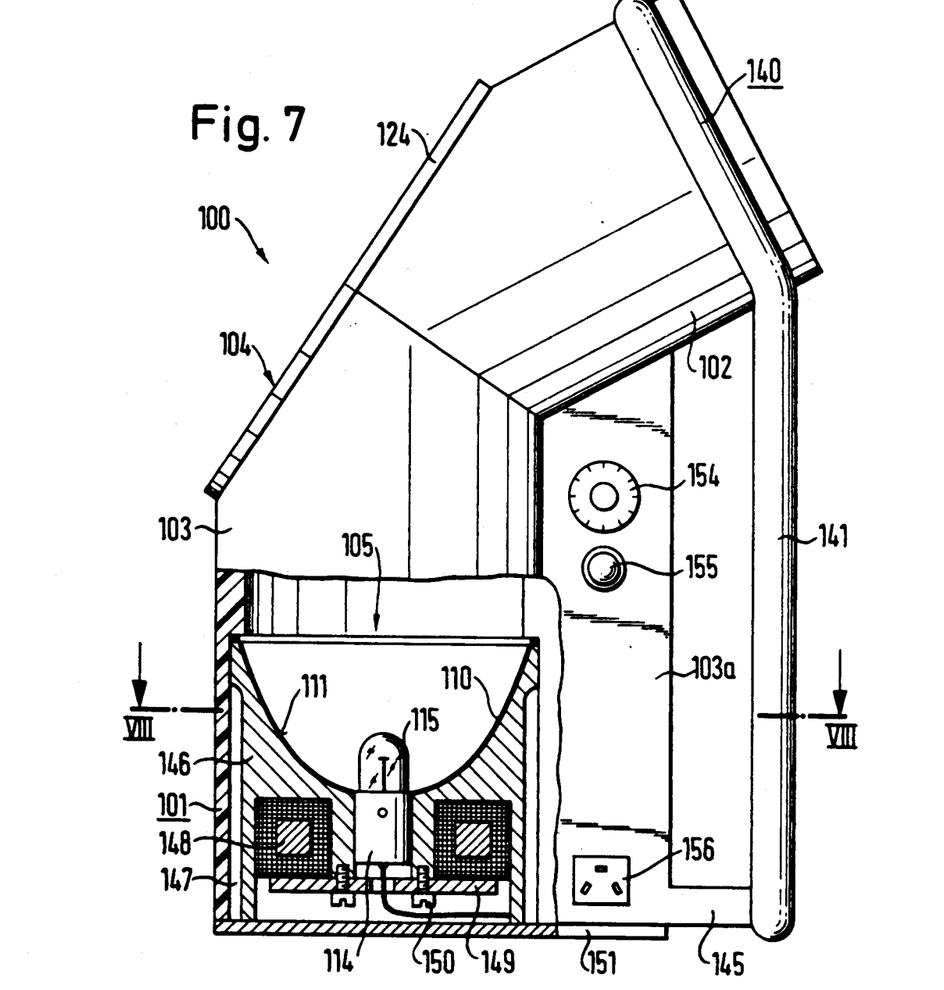
FIG. 7 shows a second embodiment of the invention, partly in section.
Figure 8:
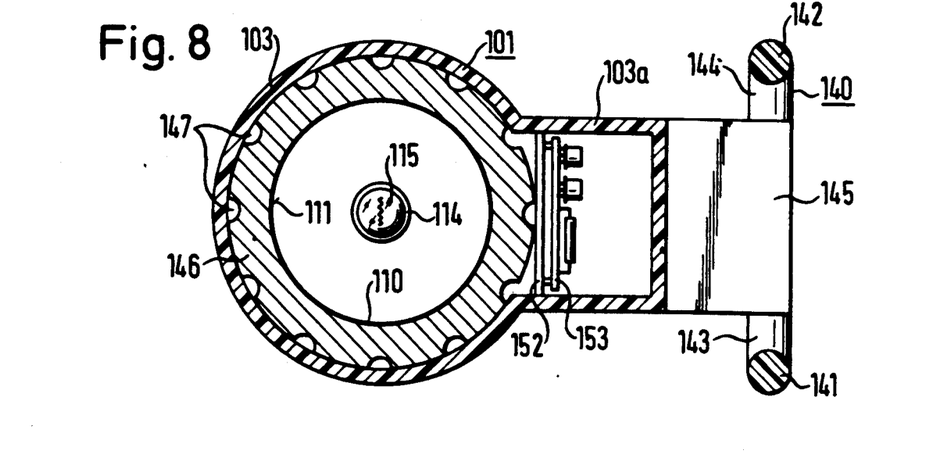
FIG. 8 is a sectional top view taken along line VIII—VIII of FIG. 7.

A second embodiment of the therapeutic lamp according to the invention is illustrated in FIGS. 7 and 8. This lamp 100 has a body or housing which can consist of two conforming and matching parts of a plastic or foam plastic material attached together to form an integral body. The housing 101 comprises a vertical tube portion 103 and a shorter tube portion 102 which has an axis that closes the twice of Brewster's angle with the axis of the vertical tube portion 103. The two portions 102, 103 are cut by a plane like in the first embodiment and a Brewster polarizer 104 is attached to the cut surface. The Brewster polarizer 104 has a design similar to that of the polarizer 4, however, the closing plate 124 thereof abuts directly the cut edge of the housing and cooling grooves extending parallel to the axis of the tubes are provided thereon instead of the cooling ribs used in the first embodiment. The tube portion 102 comprises a light filter plate similar to the plate 7 in the first embodiment.

The vertical tube 103 is substantially a hollow cylinder, however it comprises a rectangular frontal portion 103a defining an inner space communicating with that of the cylinder. The rectangular portion extends vertically up to the frontal and upper tube portion 102 and it provides a support therefor. The presence of the rectangular portion 103a increases the overall rigidity of the therapeutic lamp 100 and the hollow inner space thereof can be used for placing electronic circuits required for proper operation.

The housing has a round support and mounting bar 140 which encircles the upper half of the frontal tube portion 102 so that it is forming integral part thereof along an engagement zone and when leaving the tube portion 102 the support bar 140 has a pair of vertical legs 141, 142 spaced corresponding to the diameter of the tube portion 102 and horizontal rods 143, 144 are attached to the ends of the legs 141, 142 which end in a forward projection 145 of the rectangular portion 103a.

Such a design of the housing is preferable, since the lamp can have a stable position as shown in FIG. 7, in which the opening of the tube portion 102 is slightly inclined in upward direction, whereby for cosmetical applications the most frequent target i.e. the face of a subject can be illuminated directly so that the subject takes a very comfortable sitting position. A further advantage is the presence of the two spaced legs 141, 142 at which the lamp can be held comfortably, or a positioning device can be clamped to the legs. Last but not at least the round bar 140 lends the housing an aesthetically pleasing form.

Similarly to the first embodiment a reflector assembly 105 is provided which comprises a metal halogen light source 115, a reflector 110 with a paraboloid surface 111 and a mount 114 for the socket of the light source 115. Unlike to the first embodiment the reflector 110 is made by a thin sheet material having the form of a rotational paraboloid. A support member 146 preferably made of a die cast aluminum is provided which has a substantially paraboloid depression conforming to the rear side of the reflector 110. The reflector is attached to the member 146 e.g. by means of a heat conducting adhesive. The upper ring-like face of the support member 146 is pressed to a ring-like shoulder of the interior of the tube portion 103 via a sealing ring. Vertical grooves 147 extend along the outer surface of the member 146 which have a depth decreasing in upward direction as the wall thickness of the member gets smaller. The increased surface provided by the grooves 147 ensures sufficient cooling. The member 146 has a central bore for receiving the mount 114, the adjustment and positioning of which occurs just as it was described in connection with the first embodiment.

The lower surface of the support of the support member 146 defines a toroidal depression, in which a toroid transformer 148 can be inserted and kept. Since the light source 115 is generally a low voltage type, a mains transformer is required. If this transformer is made as a toroid one, its form is ideal for being received in the support member, whereby substantial space can be spared and there will be no need for a separate power supply unit. In the embodiment shown in FIG. 7 the transformer 148 is fixed by a ring-like pressure plate 149 clamped by bolts 150 to the support member 146. The adjustment of the mount can be made through the central opening of the plate 149 by means of an appropriate tool.

The bottom of the support member 146 defines a cylindrical inner space communicating with the torodial recess so that the transformer 148 can be inserted easily. A closure plate 151 provided preferably with cooling grooves is used to close the interior of the tube 103 and of the rectangular portion 103a. The good thermal coupling between the thin reflector and the support member 146 ensures an effective cooling, at least for the heat generated by the lamp 115 which has a power just as in the previous embodiment. Due to its small consumption and good efficiency the transformer 148 does not generate a' significant amount of heat which could influence the thermal conditions.

The vertical opening between the interiors of the tube portion 103 and rectangular portion 103a is closed by a vertical mounting plate 152 which holds a printed circuit board 153 for the components of the electronic circuits.

The electronic circuits may comprise a voltage stabilizer, a delay circuit ensuring that the current increase and decrease occurs slowly in the lamp circuit, whereby the life time of the bulb will be longer, as well as a timer by which the on-time of the lamp can be adjusted. Adjustment knob 154 of the timer, a combined on-off switch and lamp 155 and a socket 156 for the power cord can be seen in FIG. 7.

In a still further embodiment a polarizer filter of the type which is effective both in the visible and in infrared ranges can be inserted in the place of the light filter plate i.e. in the frontal end of the tube portion 102, and in that case the Brewster polarizer can be replaced by a mirror. In this embodiment the two tube portions 102, 103 need not close accurately the twice of the Brewster's angle, a similar angle is still preferable from the point of view of the comfort of the user.

The advantage of the second and third embodiments is that the paraboloid reflector can be made of a thin sheet with a cheap technology compared to the accurate machining of the surface in the first embodiment. The die-casting of the support member 146 is a cheap process and there is no need for using the specific alloy. Further advantages are the easier way of use, the convenient self-support and the lack of need for a separate power supply.

It is true for all embodiments that the therapeutic lamp according to the invention has an ergonomic design and it is capable of treating larger body areas (e.g. the whole face of a subject) in a short period of time. The closed constructional design prevents the optically active surfaces from being dusty or dirty during operation which ensures that the intensity of the output light remains unchanged during longer use.

We claim:

1. Therapeutic lamp for biostimulation with polarized light, comprising a light source with a power substantially between 30W and 300W and being substantially a point source, a reflector with a rotational paraboloid light reflecting surface defining a focal point arranged behind the light source so that said focal point substantially coinciding with said point source to reflect forward the majority of light emitted by said source in a parallel path, a polarizer arranged in said path to generate polarized output light propagating in a predetermined direction and having a cross-section of at least 100 cm$^2$, wherein said lamp further comprises a first tube with a first axis coinciding with axis of rotation of said paraboloid surface, said reflector with said light source being fixed to said first tube so that a sealed connection is provided therebetween, a second tube with a second axis closing an angle between 100° and 20° with said first axis, said tubes having substantially equal and circular cross-sections and are attached to each other to form an integral housing, both of said tubes are cut with a plane extending normal to a plane determined by said first and second axes so that said plane cuts substantially the whole cross-sections of both tubes, said cutting plane closing substantially the same angle with said first and second axis, whereby an opening with an elliptical contour line is defined, a light diverting means closing said opening for diverting light arriving from said first tube to axial direction of said second tube, said means comprising a closing plate of a heat conducting material, a light transparent plate arranged in frontal section of said second tube to close inner space thereof, and heat dissipating means for providing operational temperature for said light source, said tubes forming parts of an integral housing made preferably of a plastic material, said housing comprises a round bar encircling the frontal and upper half of said second tube and extending downwardly substantially parallel to said first axis in the form of a pair of spaced legs.

2. The therapeutic lamp as claimed in claim 1, wherein said legs are continued in rods, said first tube comprises a hollow rectangular portion extending along frontal zone thereof and ending in said second tube, a projection is extending out of the bottom of said rectangular portion to receive ends of said rods, said first tube including said reflector and said heat dissipating means and has a bottom end normal to said first axis.

3. The therapeutic lamp as claimed in claim 1, wherein a toroid transformer for supplying said light source with a small voltage is arranged in the first tube below said paraboloid surface and electronic circuits for operating the light source are arranged in the hollow space of said rectangular portion of the first tube.

4. The therapeutic lamp as claimed in claim 3, wherein said reflector is made of a thin metal sheet and said heat dissipating means comprises a member of a heat conducting metal fitting in the interior of the first tube and said member has an upper recess conforming to the shape of the rear side of the reflector and said conforming surfaces are attached to each other so that a good heat conductive coupling is established between them, cooling grooves are provided at the cylindrical outer periphery of said member, and a central bore is formed in the member for receiving a mount holding said light source, a toroidal recess is formed at the bottom of said member to receive said toroid transformer.

5. The therapeutic lamp as claimed in claim 4, wherein said electronic circuits comprise a timer for adjusting length of lighting periods of said light source and a circuit for providing delayed rising of current through the light source.

6. The therapeutic lamp as claimed in claim 4, wherein said member is made of an aluminum alloy and has a cylindrical bottom part extending to the bottom of said first tube and a metal closure plate is attached to the bottom of said first tube to close the hollow cavity thereof, said closure plate (151) is provided with cooling grooves.

7. The therapeutic lamp as claimed in claim 1, wherein said light diverting means comprises said polarizer (104) which is a Brewster polarizer, and said angle defined between the axes of the first and second tubes being twice of Brewster's angle i.e. about 114° and said transparent plate is a light filter plate transparent for wavelength components exceeding 400–450 nm.

8. The therapeutic lamp as claimed in claim 1, wherein said light diverting means comprises a mirror and said transparent plate is a polarizer filter.

9. The therapeutic lamp as claimed in claim 7, wherein said Brewster polarizer comprises a plurality of spaced thin plano-parallel glass plates substantially covering said cut opening.

10. The therapeutic lamp as claimed in claim 1, wherein said light source is a metal halogen bulb.

11. Therapeutic lamp for biostimulation with polarized light, comprising a light source with a power substantially between 30W and 300W and being substantially a point source, a reflector with a rotational paraboloid light reflecting surface defining a focal point arranged behind the light source so that said focal point substantially coinciding with said point source to reflect forward the majority of light emitted by said source in a parallel path, a polarizer arranged in said path to generate polarized output light propagating in a predetermined direction and having a cross-section of at least 100 cm², wherein said lamp further comprises a first tube with a first axis coinciding with axis of rotation of said paraboloid surface, said reflector with said light source being fixed to said first tube so that a sealed connection is provided therebetween, a second tube with a second axis closing an angle between 110° and 120° with said first axis, said tubes having substantially equal and circular cross-sections and are attached to each other to form an integral housing, both of said tubes are cut with a plane extending normal to a plane determined by said first and second axes so that said plane cuts substantially the whole cross-sections of both tubes, said cutting plane closing substantially the same angle with said first and second axis, whereby an opening with an elliptical contour line is defined, a light diverting means closing said opening for diverting light arriving from said first tube to the axial direction of said second tube, said means comprising a closing plate of a heat conducting material, a light transparent plate arranged in frontal section of said second tube to close inner space thereof, and heat dissipating means contacting said reflector for providing operational temperature for said light source, said tubes forming parts of an integral housing made preferably of a plastic material, said housing comprising a round bar encircling the frontal and upper half of said second tube and extending downwardly substantially parallel to said first axis in the form of a pair of spaced legs and continued in horizontal rods, said first tube comprising a hollow rectangular portion extending along a frontal zone thereof and ending in said second tube, a horizontal projection extending out of the bottom of said rectangular portion to receive ends of said horizontal rods, said first tube including said reflector and said heat dissipating means and which has a bottom end normal to said first axis.

* * * * *

UNITED STATES PATENT AND TRADEMARK OFFICE
CERTIFICATE OF CORRECTION

PATENT NO. : 5,010,452
DATED : April 23, 1991
INVENTOR(S) : KREBSER, et al

It is certified that error appears in the above-identified patent and that said Letters Patent is hereby corrected as shown below:

Column 9, lines 50 and 51

Amend "between 100° and 20° with said first axis" to read

--between 110° and 120° with said first axis--

Signed and Sealed this

Tenth Day of May, 1994

*Attest:*

BRUCE LEHMAN

*Attesting Officer*     *Commissioner of Patents and Trademarks*